US012735731B2

(12) United States Patent
Ma et al.

(10) Patent No.: US 12,735,731 B2
(45) Date of Patent: Sep. 15, 2026

(54) METHOD FOR PRODUCING TAGATOSE BY IMMOBILIZED MULTI-ENZYME SYSTEM

(71) Applicant: Tianjin Yeahe Biotechnology Co., Ltd, Tianjin (CN)

(72) Inventors: Yanhe Ma, Tianjin (CN); Ting Shi, Tianjin (CN); Pingping Han, Tianjin (CN)

(73) Assignee: TIANJIN YEAHE BIOTECHNOLOGY CO., LTD, Tianjin (CN)

( * ) Notice: Subject to any disclaimer, the term of this patent is extended or adjusted under 35 U.S.C. 154(b) by 321 days.

(21) Appl. No.: 18/553,371

(22) PCT Filed: Feb. 11, 2022

(86) PCT No.: PCT/CN2022/076062

§ 371 (c)(1),
(2) Date: Sep. 29, 2023

(87) PCT Pub. No.: WO2022/206189

PCT Pub. Date: Oct. 6, 2022

(65) Prior Publication Data

US 2024/0102062 A1 Mar. 28, 2024

(30) Foreign Application Priority Data

Mar. 29, 2021 (CN) ......................... 202110330594.2

(51) Int. Cl.
*C12P 19/02* (2006.01)
*C12N 9/16* (2006.01)
*C12N 9/90* (2006.01)
*C12N 9/92* (2006.01)
*C12N 11/18* (2006.01)

(52) U.S. Cl.
CPC ................ *C12P 19/02* (2013.01); *C12N 9/16* (2013.01); *C12N 9/90* (2013.01); *C12N 9/92* (2013.01); *C12N 11/18* (2013.01); *C12Y 301/03* (2013.01); *C12Y 501/03* (2013.01); *C12Y 503/01009* (2013.01); *C12Y 504/02002* (2013.01)

(58) Field of Classification Search
CPC ............ C12Y 504/02002; C12N 11/02; C12N 19/02; C12P 19/02
See application file for complete search history.

(56) References Cited

U.S. PATENT DOCUMENTS

2024/0102062 A1* 3/2024 Ma ................. C12Y 504/02002

FOREIGN PATENT DOCUMENTS

| | | | |
|---|---|---|---|
| CN | 107988286 | A | 5/2018 |
| CN | 112342179 | A | 2/2021 |
| CN | 112708616 | A | 4/2021 |
| WO | 2021011881 | A1 | 1/2021 |

OTHER PUBLICATIONS

International Searching Authority, International Search Report, International Application No. PCT/CN2022/076062 dated May 9, 2022, CN.
International Searching Authority, Written Opinion of the International Searching Authority, International Application No. PCT/CN2022/076062 dated May 9, 2022, CN.
Zhang, Bioadhesion and Biomineralization Inspired Fabrication of Multienzyme System Construction, Chinese Doctoral Dissertations Full-Text Database (Basic Sciences), Oct. 15, 2011, CN.
Han et al., Efficient multi-enzymes immobilized on porous microspheres for producing inositol from starch, Frontiers in Bioengineering & Biotechnology 8: 380 (2020).
Zhang et al., Bioinspired preparation of polydopamine microcapsule for multienzyme system construction, Green Chemistry 13(2): 300-306 (2010).
Shi et al., Polydopamine microcapsules with different wall structures prepared by a template-mediated method for enzyme immobilization, Applied Materials & Interfaces 5: 9991-9997 (2013), US.
Xu et al., Immobilization of multi-enzymes on support materials for efficient biocatalysis, Frontiers in Bioengineering & Biotechnology 8: 660 (2020).
European Patent Office, Supplementary European Search Report for EP Application No. 22778374, dated May 7, 2025, CH.

* cited by examiner

*Primary Examiner* — Tekchand Saidha
(74) *Attorney, Agent, or Firm* — Reichel Stohry Dean LLP; Natalie J. Dean

(57) ABSTRACT

Provided are a method for preparing an immobilized multi-enzyme system, and a method for producing tagatose by the immobilized multi-enzyme system. The immobilized multi-enzyme system is formed by uniformly mixing a porous dopamine microsphere with a multi-enzyme mixture which is used for producing tagatose. Five enzymes in an enzymatic catalysis path for converting starch to tagatose are co-immobilized by means of a porous microsphere to obtain an immobilized multi-enzyme system, the immobilized multi-enzyme system is used to catalyze conversion of starch into tagatose, and thus, enzymes can be recycled, thereby greatly reducing the amount of enzymes required for preparation of tagatose, and reducing the production cost.

10 Claims, 3 Drawing Sheets

METHOD FOR PRODUCING TAGATOSE BY IMMOBILIZED MULTI-ENZYME SYSTEM

PRIORITY

The present application is related to, claims the priority benefit of, and is a 35 U.S.C. 371 national stage application of International Patent Application No. PCT/CN2022/076062 filed Feb. 11, 2022, which is related to and claims priority to Chinese Patent Application No. 202110330594.2, filed Mar. 29, 2021. The content of each of the aforementioned priority applications is hereby expressly incorporated in its entirety into this disclosure by reference.

FIELD OF THE INVENTION

The present invention relates to the field of tagatose production, and specifically relates to an immobilized multi-enzyme system for producing tagatose and a method for preparing tagatose with the immobilized multi-enzymes.

BACKGROUND OF THE INVENTION

Tagatose is a naturally occurring rare monosaccharide. It is a keto form of galactose and also an epimer of fructose. It has similar sweetness characteristics with sucrose, but only one-third of the calories of sucrose, and is thus called a low-calorie sweetener. It provides very fresh and pure sweetness, with a similar taste of fructose. Research shows that tagatose has important physiologically functional properties such as low calorie, low glycemic index, anti-caries effect, antioxidation, prebiotic actions, improvement of intestinal functions, immune regulation, and use as a drug precursor. It can be widely used in food, beverages, medicine, health care and other fields, having huge economic potential. (Oh D-K: Tagatose: properties, applications, and biotechnological processes. App. Microbiol. Biotechnol. 2007, 76:1-8). Currently, a mainstream method for producing tagatose comprises steps such as galactose isomerization, desalination, decolorization, separation, concentration, and crystallization to obtain pure tagatose. However, this method has several disadvantages. The galactose cannot be completely converted into tagatose, and thus the final product is a mixture of galactose and tagatose, resulting in a low conversion rate and the need of a complex tagatose separation process. While the cost for tagatose separation is high, the galactose as a raw material is not at a low price, both contributing to a high cost for tagatose production. (Rhimi M, Aghajari N, Juy M, Chouayekh H, Maguin E, Haser R, Bejar S: Rational design of *Bacillus stearothermophilus* US100l-arabinose isomerase: Potential applications for d-tagatose production. Biochim. 2009, 91:650-653. Oh H-J, Kim H-J, Oh D-K: Increase in d-tagatose production rate by site-directed mutagenesis of 1-arabinose isomerase from *Geobacillus thermodenitrificans*. Biotechnol. Lett. 2006, 28:145-149. Bosshart A, Hee C S, Bechtold M, Schirmer T, Panke S: Directed divergent evolution of a thermostable D-tagatose epimerase towards improved activity for two hexose substrates. ChemBioChem 2015, 16:592-601.) Both the CJ corporation in Korea and the Tianjin Institute of Industrial Biotechnology, Chinese Academy of Sciences have developed a new route for producing tagatose with multiple enzymes in vitro (WO2018004310A1, CN109790524A, CN107988286A, and CN109666620A). With this route, starch, maltodextrin, or sucrose can be used as a raw material to produce tagatose through enzyme-based catalytic reactions in multiple steps. It represents a fundamental change from the existing isomerization-based tagatose production process.

However, this new route involves multiple enzyme molecules which require a plurality of steps for extraction and purification before they can be used in the catalytic reactions, resulting in a high cost for enzyme preparation. Moreover, the biological enzymes are water-soluble molecules and thus can hardly be recovered and reused after the completion of the catalytic reactions, resulting in a waste of enzymes. These factors lead to the high production cost for the new route of tagatose production. Therefore, there is an urgent need to develop a method for immobilizing multiple enzymes, which can enable the immobilization of the multiple enzymes in the new route of tagatose production, so that the enzymes can be recycled and the production cost can be lowered.

A method for preparing a porous magnetic microsphere and a carrier for immobilizing the enzyme was proposed (CN105039297A). The method had a simple preparation process with mild and green conditions. It achieved relatively high enzyme loading and relative enzyme activity by applying a porous magnetic microsphere to the immobilization of alcohol dehydrogenase. However, this method is limited to the immobilization of a single enzyme molecule, and there is no description about the effect of recycling of the immobilized enzyme. Thus, it needs further study and exploration on whether the method can be used to co-immobilize the multiple enzyme molecules in the above new route for tagatose production. Moreover, there are reports on production of tagatose using an immobilization technology. For example, Oh et al. used calcium alginate to immobilize the L-arabinose isomerase derived from *E. coli* to obtain 30 g/L tagatose within 24 h, with a conversion rate of 30%. The immobilized enzyme maintained a basically stable activity in conversion in 8 batches (Oh D K, Kim H J, Kim P, et al. Development of an immobilization method of L-arabinose isomerase for industrial production of tagatose. Biotechnology Letters, 2001, 23, 1859-1862). As another example, a method for immobilizing L-arabinose isomerase with spores of *Bacillus subtilis* was reported in 2018, wherein the immobilized enzyme can retain a residual activity of more than 85% after 20 times of recycling (CN 107937454 B). However, these reports are limited to the immobilization of L-arabinose isomerase only, and there are few reports on the immobilization of the multiple enzymes involved in the tagatose production route.

SUMMARY OF THE INVENTION

An object of the present invention is to provide a method for preparing an immobilized multi-enzyme system, an immobilized multi-enzyme system obtained therefrom, and a method for producing tagatose with the immobilized multi-enzyme system. The method for producing tagatose comprises immobilizing the multi-enzymes for enzyme-based catalytic conversion for tagatose production with a porous microsphere to obtain immobilized multi-enzymes, and producing tagatose with the immobilized multi-enzymes through catalysis. With the present invention, the enzymes can be recycled and thus the amounts of enzymes required to be added to produce tagatose in the new route can be greatly reduced, thereby reducing the production cost.

Specifically, the present invention provides a method for preparing an immobilized multi-enzyme system for producing tagatose. The immobilized multi-enzyme system is obtained by uniformly mixing a porous dopamine microsphere with a multi-enzyme mixture which is used for producing tagatose. In the present invention, a porous dopamine microsphere is used as a carrier for multi-enzyme immobilization. In terms of the structure of the carrier for multi-enzyme immobilization, a larger specific surface area of the material can provide more adsorption sites for enzyme molecules to achieve a higher loading capacity per unit mass of carrier. A higher porosity is conducive to rapid substrate transport, and thus reduction of the steric hindrance effect of the enzyme immobilized carrier on the mass transfer in reactions, ensuring the enzymes' activities in catalysis. In terms of components of the material, dopamine can provide appropriate hydrophilicity and hydrophobicity to enhance the stabilities of the immobilized multi-enzymes. In terms of recycling of enzymes, the microsphere has a relatively large particle size, and the immobilized multi-enzymes can be recycled simply by centrifugation. Thus, the amounts of the enzymes used for multi-enzyme catalysis for tagatose preparation and thus the production cost can be reduced.

The multi-enzyme mixture includes the enzymes for tagatose production, specifically, glucan phosphorylase (αGP), phosphoglucomutase (PGM), phosphoglucose isomerase (PGI), tagatose 6-phosphate 4-epimerase (T6PE) and tagatose 6-phosphate phosphatase (T6PP).

The porous dopamine microsphere can be prepared by a method comprising the following steps:

(1) pouring a sodium carbonate aqueous solution into a calcium chloride aqueous solution, stirring, carrying out solid-liquid separation, and collecting a solid product, which is a porous calcium carbonate microsphere;

(2) mixing the porous calcium carbonate microsphere with a dopamine solution, carrying out solid-liquid separation, and collecting a solid product, which is a dopamine-calcium carbonate microsphere; and (3) mixing the dopamine-calcium carbonate microsphere with ethylenediamine tetraacetic acid (EDTA) to conduct reaction (to remove calcium carbonate), carrying out solid-liquid separation, and collecting a solid product, which is the porous dopamine microsphere.

The present invention has optimized the method for preparing a porous dopamine microsphere, in which the structure, the composition and the enzyme binding force of the microsphere are modified to improve the catalysis and recycling performance of the immobilized multi-enzyme system.

In step (1) of the preparation of the porous dopamine microsphere, the concentrations of the raw materials and the stirring speed determine the basic structure and shape of the microsphere. In the present invention, the sodium carbonate aqueous solution and the calcium chloride aqueous solution preferably have the same concentration, and more preferably a concentration of 0.1-1 M. In actual operations, the sodium carbonate aqueous solution is preferably poured into an equal volume of calcium chloride aqueous solution quickly. The stirring speed in step (1) has a substantial impact on the size, shape, uniformity and the like of the microsphere, thereby affecting the catalytic effects of the immobilized multi-enzymes. In the present invention, the stirring is preferably carried out at a speed of 700-1,500 rpm, and more preferably 700-1,000 rpm.

In step (2) of the preparation of the porous dopamine microsphere, dopamine is introduced which can provide appropriate hydrophilicity and hydrophobicity to enhance the stabilities of the immobilized multi-enzymes. The present invention found through a lot of practical activities that when the ratio of the mass of dopamine in the dopamine solution to the mass of the porous calcium carbonate microsphere was 1:(3-5), preferably 1:4, the immobilized multi-enzyme system showed an excellent catalytic activity. Especially, with such a ratio, the recycling rate of the immobilized multi-enzyme system was improved, ensuring a relatively high production concentration of tagatose after multiple times of recycling of the immobilized multi-enzyme system. In practical use of the present invention, in order to increase the efficiency of dopamine binding to the porous calcium carbonate microsphere, the dopamine solution is preferably prepared by dissolving dopamine in a 40-60 mM Tris-HCl buffer at pH 8-9.

As a preferred embodiment of the present invention, the porous dopamine microsphere is prepared by a method comprising the following steps:

(1) pouring a 0.3-0.5 M sodium carbonate solution into an equal volume of 0.3-0.5 M calcium chloride solution quickly at 700-1,000 rpm, allowing a reaction for 20-40 s, washing with deionized water and then a Tris-HCl buffer, and centrifuging at 2,500-3,500 rpm for separation to obtain a porous calcium carbonate microsphere;

(2) mixing a 4-6 mg/ml solution of dopamine in Tris-HCl with the porous calcium carbonate microsphere obtained above in a volume-to-mass ratio of 100 ml:(1-3) g uniformly, stirring for 4-6 h, centrifuging at 2,500-3,500 rpm for separation, and washing solid with water until supernatant is colorless to obtain a dopamine-calcium carbonate microsphere, wherein the Tris-HCl is a 40-60 mM Tris-HCl buffer at pH 8-9; and (3) mixing the dopamine-calcium carbonate microsphere obtained above with a 40-60 mM EDTA solution uniformly (to remove calcium carbonate), centrifuging at 2,500-3,500 rpm for separation, and washing with deionized water until supernatant has no EDTA to obtain the porous dopamine microsphere.

The enzymes for tagatose production involved in the present invention comprise glucan phosphorylase (αGP), phosphoglucomutase (PGM), phosphoglucose isomerase (PGI), tagatose 6-phosphate 4-epimerase (T6PE) and tagatose 6-phosphate phosphatase (T6PP). When the above five enzymes are co-immobilized to the porous dopamine microsphere, the enzymes can be recycled with their catalytic efficiencies retained, thereby significantly reducing the cost of enzyme supply. According to the present invention, each gram of the porous dopamine microsphere is preferably attached with 1,500-2,500 U of glucan phosphorylase, 1,500-2,500 U of phosphoglucomutase, 1,500-2,500 U of phosphoglucose isomerase, 1,500-2,500 U of tagatose 6-phosphate 4-epimerase, and 1,500-2,500 U of tagatose 6-phosphate phosphatase; more preferably, each gram of the porous dopamine microsphere is attached with 2,000 U of glucan phosphorylase, 2,000 U of phosphoglucomutase, 2,000 U of phosphoglucose isomerase, 2,000 U of tagatose 6-phosphate 4-epimerase, and 2,000 U of tagatose 6-phosphate phosphatase, so as to ensure that a desired catalytic efficiency and recycling of the immobilized multi-enzymes can be realized when appropriate amounts of immobilized multi-enzymes are added in practical production of tagatose.

To ensure an even distribution of the multi-enzymes on the microsphere, the immobilized multi-enzymes can be obtained by mixing and stirring well the porous dopamine microsphere and a solution of multi-enzyme mixture which is used for producing tagatose. As a preferred embodiment of the present invention, the solution of multi-enzyme mixture contains 1.5-2.5 U/ml of glucan phosphorylase, 1.5-2.5 U/ml of phosphoglucomutase, 1.5-2.5 U/ml of phosphoglucose isomerase, 1.5-2.5 U/ml of tagatose 6-phosphate 4-epimerase and 1.5-2.5 U/ml of tagatose 6-phosphate phosphatase. Preferably, it contains 2 U/ml of glucan phosphorylase, 2 U/ml of phosphoglucomutase, 2 U/ml of phosphoglucose isomerase, 2 U/ml of tagatose 6-phosphate 4-epimerase and 2 U/ml of tagatose 6-phosphate phosphatase. The porous dopamine microsphere and the solution of multi-enzyme mixture are in a mass-to-volume ratio of 1 g:(1.5-2.5) L.

The present invention also provides an immobilized multi-enzyme system obtained by the above preparation method. The present invention further provides a method for producing tagatose with the immobilized multi-enzyme system, wherein the method comprises using starch or a starch derivative as a raw material, and carrying out enzyme-based catalytic conversion with the immobilized multi-enzyme system to produce tagatose.

As a preferred embodiment of the present invention, the method specifically comprises taking 50-150 g/L of starch or starch derivative, an 80-120 mM HEPES buffer at pH 6.0-7.0, 10-50 mM inorganic phosphate, 3-7 mM divalent magnesium ions, 0.3-0.7 mM zinc ions or manganese ions, 3-7 U/ml of debranching enzyme, and 3-7 mg immobilized multi-enzymes/ml reaction liquid; carrying out enzyme-based catalytic conversion reactions at 40-70° C.; and collecting tagatose. The starch derivative is, for example, maltodextrin, amylose, amylopectin, or oligosaccharide.

After the above reactions are completed, solid-liquid separation is carried out to collect the immobilized multi-enzymes, which can be recycled for the preparation of inositol. The immobilized multi-enzymes can maintain relatively high catalytic activities when they are recycled for 1-9 times, preferably 1-7 times.

Compared with the prior art, the immobilized multi-enzyme system for producing tagatose prepared by the present invention has excellent catalytic activities and stabilities, especially, the enzymes can be recovered simply by centrifugation. Use of the porous dopamine microsphere-immobilized multi-enzyme system in tagatose production enables a simple process with mild conditions and recycling of the enzymes. It can greatly reduce the amounts of enzymes required to be added to prepare tagatose in multiple cycles and thereby lower the production cost.

DETAILED DESCRIPTION OF THE INVENTION

Figure 1:
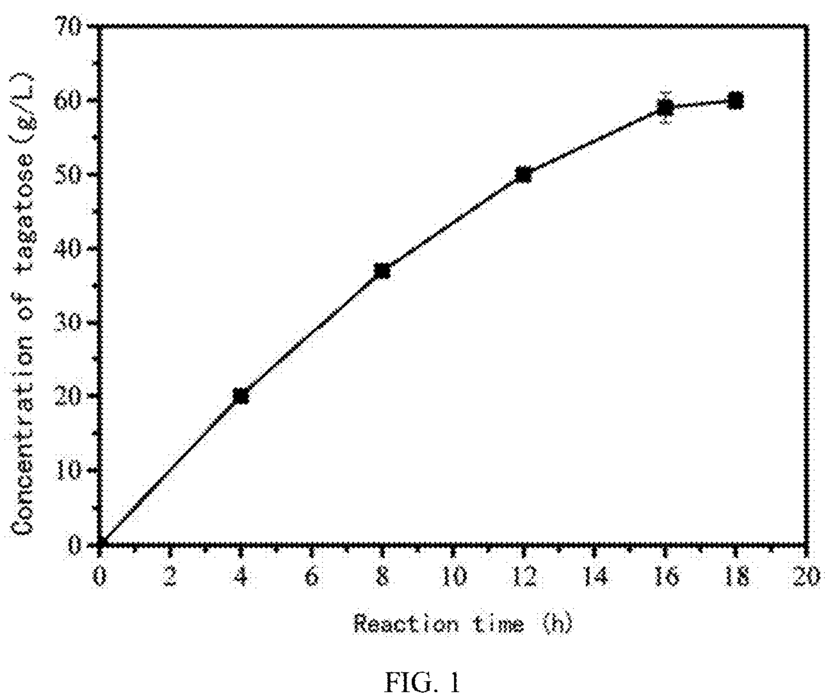
FIG. 1 is the conversion curve for tagatose preparation with the immobilized multi-enzyme system provided by Example 1.

The present invention discloses a method for producing tagatose with an immobilized multi-enzyme system. A person skilled in the art can, referring to the contents of the present invention, appropriately modify the parameters for implementation of the processes. Noted that all similar replacements or modifications are apparent to a person skilled in the art and are considered within the scope of the present invention. The methods of the present invention have been described through preferred embodiments. It is apparent that relevant personnel can modify or appropriately change and combine the methods and applications described herein to implement or apply the technology of the present invention without departing from the content, spirit, and scope of the present invention.

Example 1

In this example, a porous dopamine microsphere was prepared by the following method.

(1) A calcium chloride aqueous solution and a sodium carbonate aqueous solution were prepared at 0.33 M respectively. The sodium carbonate solution was quickly poured into an equal volume of the calcium chloride solution at 700 rpm and a reaction was allowed to carry out for 30 s. Deionized water and then a Tris-HCl buffer were used for washing. Centrifugation was carried out at 3,000 rpm for separation to obtain a porous calcium carbonate microsphere.

(2) A 6 mg/ml solution of dopamine in Tris-HCl was prepared, wherein the Tris-HCl was a 50 mM Tris-HCl buffer at pH 8.5. Two hundred (200) ml of dopamine solution was mixed with 3.5 g of the porous calcium carbonate microsphere obtained above uniformly, stirred for 5 h, and centrifuged at 3,000 rpm for separation. Water was used for washing until a supernatant was colorless to obtain a dopamine-calcium carbonate microsphere.

(3) The dopamine-calcium carbonate microsphere obtained above was mixed with a 50 mM EDTA solution uniformly to remove calcium carbonate. Centrifugation was carried out at 3,000 rpm for separation, and deionized water was used for washing until a supernatant contained no EDTA to obtain a porous dopamine microsphere, which was a carrier for enzyme immobilization.

The porous dopamine microsphere prepared above was used to prepare an immobilized multi-enzyme system. Specifically, 200 ml of a solution of multi-enzyme mixture and 3.5 g of the porous dopamine microsphere were mixed and stirred at 300 rpm for 2.5 h to obtain the system. The solution of multi-enzyme mixture contained 2 U/ml of glucan phosphorylase, 2 U/ml of phosphoglucomutase, 2 U/ml of phosphoglucose isomerase, 2 U/ml of tagatose 6-phosphate 4-epimerase, and 2 U/ml of tagatose 6-phosphate phosphatase.

Example 2

Compared with Example 1, this example was different only in that, in step (2), the dopamine had a mass concentration of 2 mg/ml instead of 6 mg/ml.

Example 3

Compared with Example 1, this example was different only in that, in step (1), the sodium carbonate solution was quickly poured into an equal volume of the calcium chloride solution at 1,500 rpm.

Comparative Example 1

This comparative example provided a non-immobilized multi-enzyme mixture which had the same composition as the solution of multi-enzyme mixture of Example 1.

Comparative Example 2

This comparative example provided a mixture of immobilized single enzymes for tagatose production. Compared with Example 1, this example was different only in that glucan phosphorylase, phosphoglucomutase, phosphoglucose isomerase, tagatose 6-phosphate 4-epimerase, and tagatose 6-phosphate phosphatase were respectively immobilized on the porous dopamine microsphere, and then theses five immobilized single enzymes were mixed. The amount of each enzyme, the amount of the porous dopamine microsphere and the specific method for immobilization were the same as those in Example 1.

Example 4

The immobilized multi-enzymes provided by Examples 1-3, the multi-enzyme mixture provided by Comparative Example 1 or the mixture of immobilized single enzymes provided by Comparative Example 2 were respectively used to prepare tagatose using the following method.

A hundred (100) g/L of starch, 100 mM HEPES buffer at pH 6.5, 40 mM inorganic phosphate, 5 mM divalent magnesium ions, 0.5 mM zinc ions or manganese ions, 5 U/ml of debranching enzyme, 5 U/ml of the immobilized multi-enzymes or the non-immobilized multi-enzyme mixture or the mixture of immobilized single enzymes provided by any of the above Examples or the Comparative Examples were taken. Reactions were carried out at 70° C. The concentration of tagatose was determined by high performance liquid chromatography (HPLC).

When the immobilized multi-enzymes provided by Example 1 were used for preparation, after 18 hours of reaction, 60.2 g/L of tagatose was produced with a conversion rate of 60.2%. The tagatose production concentration within 18 h was shown in FIG. 1. Compared with the multi-enzyme mixture provided by Comparative Example 1, the immobilized multi-enzymes resulted in a slightly lower conversion rate in preparation. This was due to the immobilization which caused reduced enzyme activities. Compared with Comparative Example 2, the immobilized multi-enzymes led to a significantly advantageous conversion rate, demonstrating that co-immobilization of multi-enzymes facilitated substrate transfer.

When the immobilized multi-enzymes provided by Example 2 was used for preparation, after 18 hours of reaction, 54.1 g/L of tagatose was produced with a conversion rate of 54.1%. Compared with the immobilized multi-enzymes provided by Example 1, the immobilized multi-enzymes provided by Example 2 resulted in a lower conversion rate in preparation. This may be due to that an excessively high concentration of dopamine would lead to a reduced porosity of the carrier for immobilization, thereby reducing the activities of immobilized multi-enzymes.

When the immobilized multi-enzymes provided by Example 3 was used for preparation, after 18 hours of reaction, 48.4 g/L of tagatose was produced with a conversion rate of 48.4%. Compared with the immobilized multi-enzymes provided by Example 1, the immobilized multi-enzymes provided by Example 3 resulted in a lower conversion rate in preparation. This may be due to that an increased stirring speed during preparation of a carrier for immobilization would reduce the particle size and porosity of the carrier for immobilization, thereby reducing the activities of the immobilized multi-enzymes.

Figure 2:
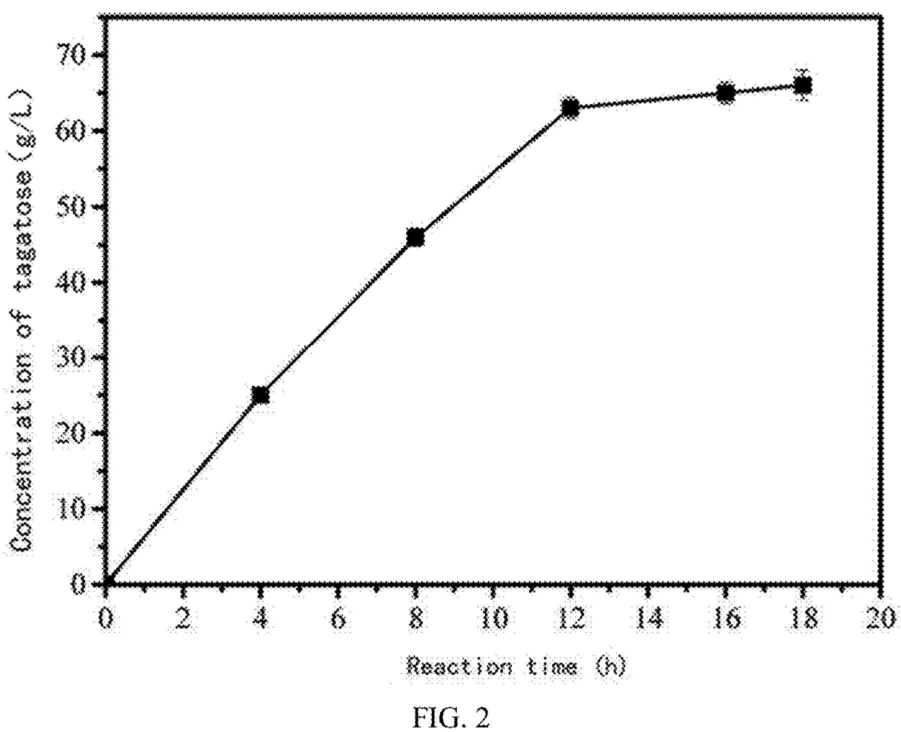
FIG. 2 is the conversion curve for tagatose preparation with the non-immobilized multi-enzyme mixture provided by Comparative Example 1.

When the multi-enzyme mixture provided by Comparative Example 1 was used for preparation, after 18 hours of reaction, 66.7 g/L of tagatose was produced with a conversion rate of 66.7%. The tagatose production concentration within 18 h was shown in FIG. 2.

Figure 3:
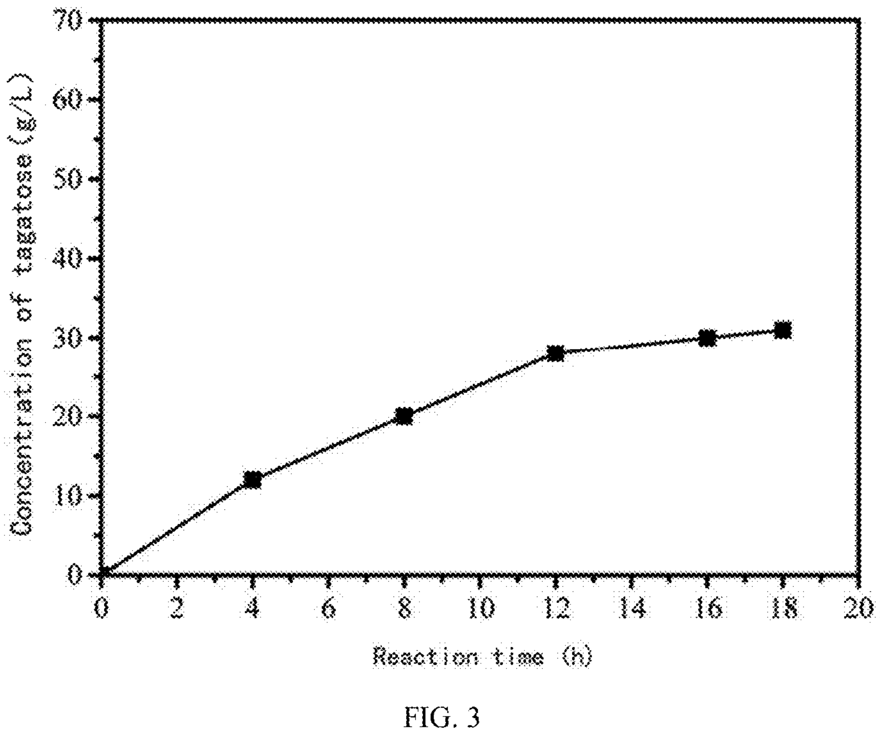
FIG. 3 is the conversion curve for tagatose preparation with the mixture of immobilized single enzymes provided by Comparative Example 2.

When the mixture of immobilized single enzymes provided by Comparative Example 2 was used for preparation, after 18 hours of reaction, 31.2 g/L of tagatose was produced with a conversion rate of 31.2%. The tagatose production concentration within 18 h was shown in FIG. 3. Compared with the immobilized multi-enzymes provided by Example 1, the mixture of immobilized single enzymes provided by Comparative Example 2 resulted in a lower conversion rate in preparation due to mass transfer. Compared with the co-immobilized multi-enzymes, the immobilized single enzymes which were mixed before preparation had a lower mass transfer effect for substrates, thus leading to a reduced conversion rate with Comparative Example 2. Compared with the catalytic reactions with the non-immobilized multi-enzymes of Comparative Example 1, the catalytic reactions with the mixed immobilized single enzymes of Comparative Example 2 led to a lower conversion rate, as activities of enzymes were lowered after immobilization.

Example 5

Tagatose was prepared with the method provided by Example 4, and then solid-liquid separation was carried out. The immobilized multi-enzymes were collected and recycled for the preparation of tagatose according to the same method. The tagatose production concentration in each cycle was determined by HPLC. The results were expressed as relative tagatose production concentration. The tagatose production concentration in the first cycle of reactions was set as 100%.

Figure 4:
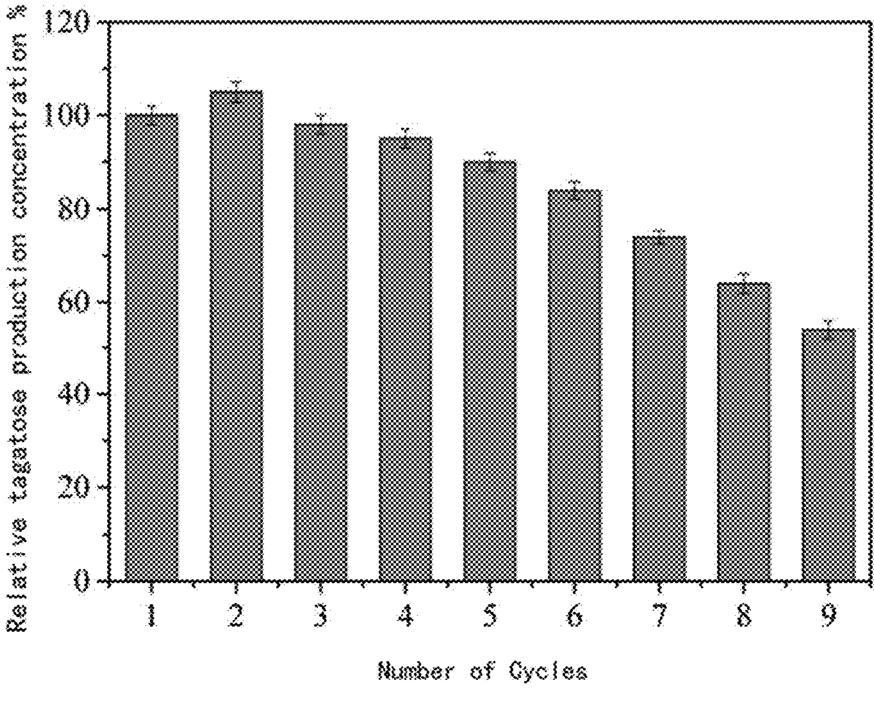
FIG. 4 is a column chart showing the multiple recycles of the immobilized multi-enzyme system provided by Example 1 for tagatose preparation.

Preparation was carried out with the immobilized multi-enzyme system provided by Example 1. After 9 cycles, the recycled immobilized multi-enzymes resulted in a relative tagatose production concentration of 54.1%, as shown in FIG. 4.

Figure 5:
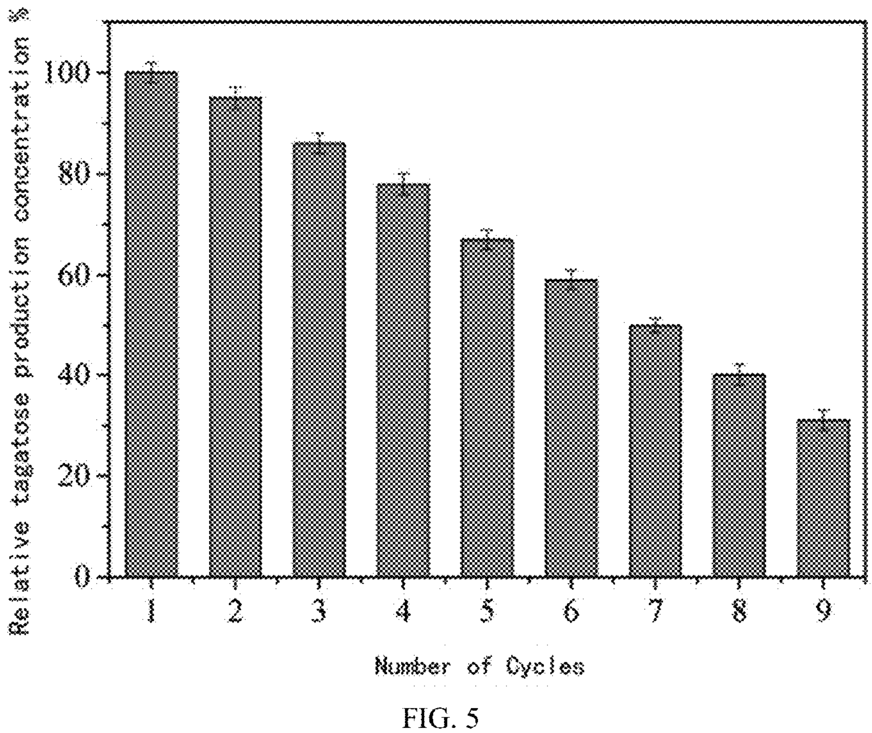
FIG. 5 is a column chart showing the multiple recycles of the immobilized multi-enzyme system provided by Example 2 for tagatose preparation.

Preparation was carried out with the immobilized multi-enzyme system provided by Example 2. After 9 cycles, the recycled immobilized multi-enzymes resulted in a relative tagatose production concentration of 31.2%, as shown in FIG. 5.

Figure 6:
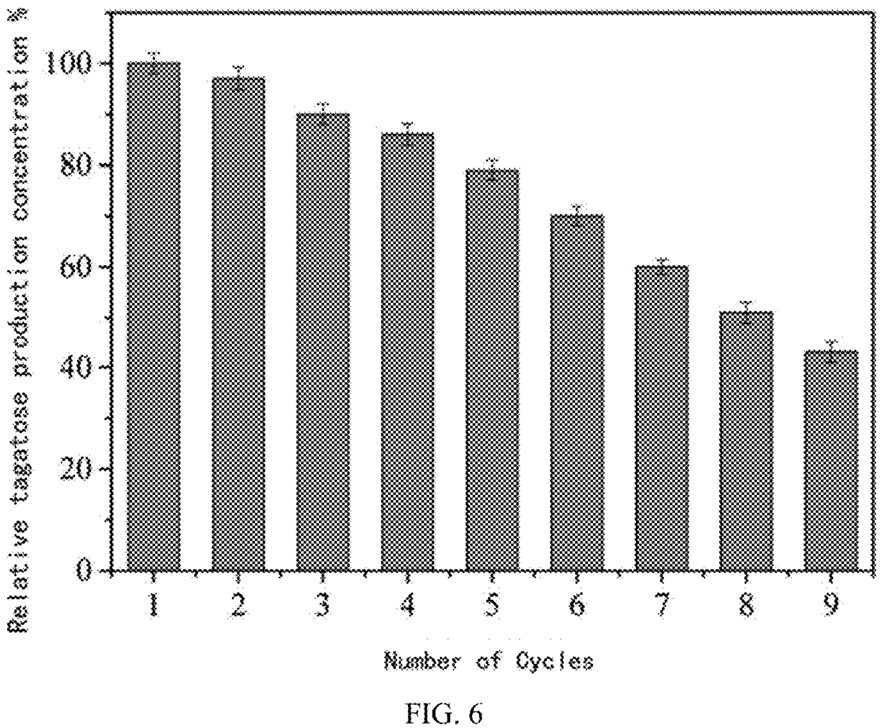
FIG. 6 is a column chart showing the multiple recycles of the immobilized multi-enzyme system provided by Example 3 for tagatose preparation.

Preparation was carried out with the immobilized multi-enzyme system provided by Example 3. After 9 cycles, the recycled immobilized multi-enzymes resulted in a relative tagatose production concentration of 43.0%, as shown in FIG. 6.

Preparation was carried out with the mixture of immobilized single enzymes provided by Comparative Example 2. After 9 cycles, the recycled immobilized multi-enzymes resulted in a relative tagatose production concentration of 15.1%.

Note that, since the non-immobilized multi-enzymes provided by Comparative Example 1 were hard to be recovered and reused after one cycle of reactions for preparation, recycling was not carried out with the enzymes of Comparative Example 1. This also explained the advantages of enzyme immobilization.

Although the present invention has been described in detail with general description, embodiments, and experiments above, it is obvious to a person skilled in the art that some modifications or improvements can be made based on the present invention. Therefore, these modifications or improvements made without departing from the spirit of the present invention are within the claimed scope of the present invention.

The invention claimed is:

1. A method for preparing an immobilized multi-enzyme system, characterized in that the immobilized multi-enzyme system is prepared by uniformly mixing a porous polydopamine microsphere with a multi-enzyme mixture which is used for producing tagatose; the multi-enzyme mixture comprises glucan phosphorylase, phosphoglucomutase, phosphoglucose isomerase, tagatose 6-phosphate 4-epimerase and tagatose 6-phosphate phosphatase; the enzymes of the multi-enzyme mixture are attached in an amount as follows, that is, each gram of the porous polydopamine microsphere is attached with 1,500-2,500 U of glucan phosphorylase, 1,500-2,500 U of phosphoglucomutase, 1,500-2,500 U of phosphoglucose isomerase, 1,500-2,500 U of tagatose 6-phosphate 4-epimerase, and 1,500-2,500 U of tagatose 6-phosphate phosphatase;

the porous polydopamine microsphere is prepared by a method comprising the following steps:

(1) pouring a sodium carbonate aqueous solution into a calcium chloride aqueous solution, stirring, carrying out solid-liquid separation, and collecting a solid product, which is a porous calcium carbonate microsphere;

(2) mixing the porous calcium carbonate microsphere with a dopamine solution, carrying out solid-liquid separation, and collecting a solid product, which is a polydopamine-calcium carbonate microsphere; and (3) mixing the polydopamine-calcium carbonate microsphere with ethylenediamine tetraacetic acid (EDTA) to conduct reaction, carrying out solid-liquid separation, and collecting a solid product, which is the porous polydopamine microsphere.

2. The method according to claim 1, characterized in that in step (1), the sodium carbonate aqueous solution and the calcium chloride aqueous solution have the same concentration.

3. The method according to claim 1, characterized in that in step (1), the stirring is carried out at a speed of 700-1,500 rpm.

4. The method according to claim 1, characterized in that in step (2), the ratio of the mass of dopamine in the dopamine solution to the mass of the porous calcium carbonate microsphere is 1:(3-5).

5. The method according to claim 4, characterized in that the dopamine solution is prepared by dissolving dopamine in a 40-60 mM Tris-HCl buffer at pH 8-9.

6. The method according to claim 1, characterized in that the porous polydopamine microsphere is prepared by a method comprising the following steps:

(1) pouring a 0.3-0.5 M sodium carbonate aqueous solution into an equal volume of 0.3-0.5 M calcium chloride aqueous solution quickly at 700-1,000 rpm, allowing a reaction for 20-40 s, washing with deionized water and then a Tris-HCl buffer, and centrifuging at 2,500-3,500 rpm for separation to obtain a porous calcium carbonate microsphere;

(2) mixing a 4-6 mg/ml solution of dopamine in Tris-HCl with the porous calcium carbonate microsphere obtained above in a volume-to-mass ratio of 100 ml:(1-3) g uniformly, stirring for 4-6 h, centrifuging at 2,500-3,500 rpm for separation, and washing solid with water until supernatant is colorless to obtain a dopamine calcium carbonate microsphere, wherein the Tris-HCl is a 40-60 mM Tris-HCl buffer at pH 8-9; and (3) mixing the polydopamine-calcium carbonate microsphere obtained above with a 40-60 mM EDTA solution uniformly, centrifuging at 2,500-3,500 rpm for separation, and washing with deionized water until supernatant has no EDTA to obtain the porous polydopamine microsphere.

7. The method according to claim 1, characterized in that the immobilized multi-enzymes are obtained by mixing the porous polydopamine microsphere with a solution of multi-enzyme mixture which is used for producing tagatose in a mass-to-volume ratio of 1 g:(1.5-2.5) L and stirring, wherein the solution of multi-enzyme mixture contains 1.5-2.5 U/ml of glucan phosphorylase, 1.5-2.5 U/ml of phosphoglucomutase, 1.5-2.5 U/ml of phosphoglucose isomerase, 1.5-2.5 U/ml of tagatose 6-phosphate 4-epimerase and 1.5-2.5 U/ml of tagatose 6-phosphate phosphatase.

8. An immobilized multi-enzyme system prepared by the method according to claim 1.

9. A method for producing tagatose with the immobilized multi-enzyme system according to claim 8, characterized in that the method comprises using starch or a starch derivative as a raw material, and carrying out enzyme-based catalytic conversion with the immobilized multi-enzyme system to prepare tagatose.

10. The method according to claim 9, characterized in that specific steps comprise taking 50-150 g/L of starch or starch derivative, an 80-120 mM HEPES buffer at pH 6.0-7.0, 10-50 mM inorganic phosphate, 3-7 mM divalent magnesium ions, 0.3-0.7 mM zinc ions or manganese ions, 3-7 U/ml of debranching enzyme, and 3-7 mg/ml of immobilized multi-enzymes to form a reaction liquid, carrying out enzyme-based catalytic conversion reaction at 40-70° C., and collecting tagatose.

* * * * *